(12) United States Patent
Hu et al.

(10) Patent No.: US 10,722,189 B2
(45) Date of Patent: Jul. 28, 2020

(54) SYSTEM AND METHOD FOR WHOLE BODY CONTINUOUS BED MOTION PARAMETRIC PET WITH FLEXIBLE SCAN MODES (71) Applicant: Siemens Medical Solutions USA, Inc., Malvern, PA (US)

(72) Inventors: Jicun Hu, Knoxville, TN (US); Vladimir Y. Panin, Knoxville, TN (US); Anne M. Smith, Lenoir City, TN (US); William Curtis Howe, Knoxville, TN (US); Vijay Shah, Knoxville, TN (US); Frank Kehren, Knoxville, TN (US); Michael E. Casey, Louisville, TN (US); Matthew Baker, Knoxville, TN (US); Bernard Bendriem, Knoxville, TN (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 471 days.

(21) Appl. No.: 15/690,885

(22) Filed: Aug. 30, 2017

(65) Prior Publication Data

US 2019/0059831 A1    Feb. 28, 2019

(51) Int. Cl.
*A61B 6/03* (2006.01)
*G06T 11/00* (2006.01)
(Continued)

(52) U.S. Cl.
CPC .............. *A61B 6/037* (2013.01); *A61B 6/027* (2013.01); *A61B 6/0457* (2013.01); *A61B 6/503* (2013.01);
(Continued)

(58) Field of Classification Search
CPC ....... G06T 11/005; A61B 6/037; A61B 3/507; A61B 6/027; A61B 6/0457; A61B 6/5205; A61B 6/5217; A61B 6/503
See application file for complete search history.

(56) References Cited

U.S. PATENT DOCUMENTS

| 6,915,004 B2 | 7/2005 | Newport et al. |
| 9,262,844 B2 | 2/2016 | Hu et al. |

(Continued)

FOREIGN PATENT DOCUMENTS

| JP | H02134589 A | 5/1990 |
| WO | 2012167257 A1 | 12/2012 |
| WO | 2015019312 A1 | 2/2015 |

OTHER PUBLICATIONS

Patlak, Clifford S. et al., "Graphical Evaluation of Blood-to-Brain Transfer Constants from Multiple-Time Uptake Data. Generalizations" Journal of Cerebral Blood Flow and Metabolism, 1985, pp. 584-590, vol. 5, No. 4.

(Continued)

*Primary Examiner* — Hien N Nguyen (57) ABSTRACT

A method of processing and reconstructing dynamic positron emission tomography (PET) sinogram data comprises: acquiring PET sinogram data using continuous bed motion having a varying velocity; recording a plurality of position-time coordinate pairs while acquiring the PET sinogram data; determining respective acquisition times of each of a plurality of slices of the image, based on the plurality of position-time coordinates; and reconstructing respective parametric images for each respective slice in the plurality of slices.

15 Claims, 11 Drawing Sheets

(51) Int. Cl.
*A61B 6/00* (2006.01)
*A61B 6/02* (2006.01)
*A61B 6/04* (2006.01)

(52) U.S. Cl.
CPC ............ *A61B 6/507* (2013.01); *A61B 6/5205* (2013.01); *A61B 6/5217* (2013.01); *G06T 11/005* (2013.01)

(56) References Cited

U.S. PATENT DOCUMENTS

| | | | |
|---|---|---|---|
| 2010/0074498 A1 | 3/2010 | Breeding et al. | |
| 2012/0308106 A1* | 12/2012 | Kelly | G06T 7/20 382/131 |
| 2014/0200848 A1* | 7/2014 | Panin | A61B 6/037 702/179 |
| 2015/0302613 A1* | 10/2015 | Hu | G06T 11/003 382/131 |

OTHER PUBLICATIONS

Panin, V. Y. et al., "Continuous bed motion on clinical scanner: design, data correction, and reconstruction" Phys. Med. Biol., Oct. 2014, 59, pp. 6153-6174.

Osborne, Dustin R. et al., "Quantitative and qualitative comparison of continuous bed motion and traditional step and shoot PET/CT" Am J Nucl Med Mol Imaging. 2015; 5(1): pp. 56-64.

Bömert, Peter et al., "Principles of Whole-Body Continuously-Moving-Table MRI" Journal of Magnetic Resonance Imaging 28:1-12 (2008).

Vriens, Dennis et al., "A Curve-Fitting Approach to Estimate the Arterial Plasma Input Function for the Assessment of Glucose Metabolic Rate and Response to Treatment" J Nucl Med., Dec. 2009; 50(12):1933-1939.

Panin, V. Y. et al., "Whole Body Parametric Imaging on Clinical Scanner: Direct 4D Reconstruction with Simultaneous Attenuation Estimation and Time-Dependent Normalization" 2015 IEEE Nuclear Science Symposium and Medical Imaging Conference, NSS/MIC 2015, Oct. 3, 2016, pp. 1-7, Institute of Electrical and Electronics Engineers Inc.

Wang, Guobao et al., "Acceleration of Direct Reconstruction of Linear Parametric Images Using Nested Algorithms" Phys Med Biol. Mar. 7, 2010; 55(5): pp. 1505-1517.

Patlak, Clifford S. et al., "Graphical Evaluation of Blood-to-Brain Transfer Constants from Multiple-Time Uptake Data" Journal of Cerebral Blood Flow and Metabolism, 1983, pp. 1-7, vol. 3, No. 1.

Karakatsanis, Nicolas A. et al., "Direct 4D slice-wise whole-body parametric PET image reconstruction for continuous bed motion acquisitions" 2016 IEEE Nuclear Science Symposium and Medical Imaging Conference, Strasbourg, France, pp. 1-6.

Karakatsanis, Nicolas A. et al., "Whole-body direct 4D parametric PET imaging employing nested generalized Patlak expectation—maximization reconstruction" Phys. Med. Biol. 61 (2016) 5456-5485.

Hu, Jicun et al., "Clinical whole body CBM parametric PET with flexible scan modes" submitted to the IEEE Medical Imaging Conference 2017.

* cited by examiner

SYSTEM AND METHOD FOR WHOLE BODY CONTINUOUS BED MOTION PARAMETRIC PET WITH FLEXIBLE SCAN MODES

FIELD

This disclosure relates generally to medical imaging, and more specifically to parametric imaging with continuous bed motion positron emission tomography.

BACKGROUND

Positron emission tomography (PET) is a modality of nuclear medicine for imaging metabolic processes by employing gamma photons emanated from radiopharmaceuticals ingested by a patient or injected into a patient. Multiple PET images are taken in multiple directions to generate/reconstruct a 3-dimensional PET image and/or multiple slices of a PET image. Before image reconstruction, PET raw image data are in projection/sinogram space. PET scanning generally provides useful information regarding the functional condition of the body tissues and systems such as the cardiovascular system, respiratory system, and/or other systems. PET scanning is useful for indicating the presence of soft tissue tumors or decreased blood flow to certain organs or areas of the body. Typically, a large number of PET data acquisitions (e.g., frames) are acquired at multiple bed positions during the imaging period.

Parametric PET imaging aims to image tracer kinetics over time based on dynamic data and has the potential to provide more information for tissue pathology than traditional standard uptake value (SUV) imaging. Blood input function, which characterize the concentration of radiopharmaceutical in the blood over time, is a key component in parametric PET. The blood input function can be obtained from a PET scanner using an image based method or provided by users through population based method.

A PET scanner has a limited field of view (FOV) smaller than the height of a patient's whole body. Recently, continuous bed motion (CBM) PET systems have been proposed. A CBM PET system is capable of acquiring whole body images. In CBM systems, the bed is moved with respect to the PET scanner. For example is moved from a start position, for example, head-first, to an end position, for example, the feet of a patient, at a constant rate. PET data are collected continuously from the start position to the end position.

Unlike volume images obtained by step and shoot scan, axial slices in an image obtained in a CBM scan have different time information. In CBM PET, the bed is moving while data are acquired, so the data from every axial slice are acquired at different time relative to injection, and kinematic components of the uptake model may be affected. If bed motion effects are not accounted for properly, this may cause image non-uniformity and incorrect quantification to occur. This increases the complexity of CBM PET image processing.

SUMMARY

In some embodiments, a method of processing and reconstructing dynamic positron emission tomography (PET) sinogram data, comprises: acquiring PET sinogram data using continuous bed motion having a varying velocity; recording a plurality of position-time coordinate pairs while acquiring the PET sinogram data; determining respective slice acquisition times of each of a plurality of slices of an image, based on the plurality of position-time coordinate pairs; and reconstructing respective parametric images for each respective slice in the plurality of slices.

In some embodiments, a system for processing dynamic positron emission tomography (PET) sinogram data, comprises: a processor capable of executing instructions; and a non-transitory, machine-readable storage medium encoded with program code and coupled to the processor. The storage medium comprises: code for controlling a PET scanner to acquire PET sinogram data using continuous bed motion having a varying velocity; code for recording a plurality of position-time coordinate pairs while the PET scanner acquires the PET sinogram data; code for determining respective acquisition times of each of a plurality of slices of the image, based on the plurality of position-time coordinates; and code for reconstructing respective parametric images for each respective slice in the plurality of slices.

In some embodiments, a non-transitory, machine-readable storage medium is encoded with program code for processing dynamic positron emission tomography (PET) sinogram data, comprising: code for controlling a PET scanner to acquire PET sinogram data using continuous bed motion having a varying velocity; code for recording a plurality of position-time coordinate pairs while the PET scanner acquires the PET sinogram data; code for determining respective acquisition times of each of a plurality of slices of the image, based on the plurality of position-time coordinates; and code for reconstructing respective parametric images for each respective slice in the plurality of slices.

DETAILED DESCRIPTION

This description of the exemplary embodiments is intended to be read in connection with the accompanying drawings, which are to be considered part of the entire written description. In the description, relative terms such as "lower," "upper," "horizontal," "vertical,", "above," "below," "up," "down," "top" and "bottom" as well as derivative thereof (e.g., "horizontally," "downwardly," "upwardly," etc.) should be construed to refer to the orientation as then described or as shown in the drawing under discussion. These relative terms are for convenience of description and do not require that the apparatus be constructed or operated in a particular orientation. Terms concerning attachments, coupling and the like, such as "connected" and "interconnected," refer to a relationship wherein structures are secured or attached to one another either directly or indirectly through intervening structures, as well as both movable or rigid attachments or relationships, unless expressly described otherwise.

Accurate imaging time information is important for accurate results of parametric PET since kinetics parameters, for example, metabolism rate, are closely correlated to time information. Therefore, for a PET system that is able to perform parametric imaging, it is very desirable to have a mechanism to track the time information of the dynamic scan procedure and to synchronize blood input function and dynamic PET data.

Clinical positron emission tomography (PET) scanners with continuous bed motion (CBM) offer great flexibility to acquire dynamic data for parametric imaging in terms of scan range, scan direction, and scan speed compared to step and shoot acquisition. In various embodiments described herein, using CBM, the technician can perform multi-pass dynamic scans with a variety of scan modes. CBM scanning modes may include, but are not limited to: single-direction, multi-scan motion, bidirectional motion, or combinations of single-direction, multi-scan motion during a first portion of a scan and bidirectional motion during a second portion of the pass. Each of these scanning modes can include a variety of velocity profiles.

Ideally, parametric images obtained by different scan modes should be identical since underlying physiology is independent of the scan. However, it is challenging to get consistent quantification results for parametric images among different dynamic CBM scan modes, if scans are not accurately tracked and time information is not properly taken into account.

This disclosure provides a method to calculate image slice reference time of different scan passes for parametric PET based on finely sampled "bed tags". Bed tags are coordinate pairs accurately encoding position and time information of the bed throughout the scan. In the exemplary CBM PET system, the velocity and/or acceleration of the patient's bed (also referred to as a table) can be constant, or can vary over time, so the position of the bed as a function of time is not easily calculated. Thus, two different axial slices can have respectively different imaging-start times, different durations, and different basis functions. In some embodiments, bed tags are recorded periodically, providing an accurate record of position versus time. For example, a bed tag can be recorded at a fixed interval, such as every 100 msec.

In most instances, the slice boundaries and slice midpoints are different from the times and positions at which the bed tags are recorded. For each image slice, the imaging start time is computed as the point when the slice enters the scanner field of view (FOV), based on bed tags. Similarly, for each image slice, the imaging end time is computed as the point when the slice leaves the scanner FOV, based on bed tags. The imaging duration of the slice is defined as the difference between the imaging start time and imaging end time for the slice. The image slice reference time is then calculated as the time point when the average activity occurs due to tracer decay, while assuming no activity change due to tracer kinetics over that time duration. This slice reference time is used to obtain the blood input function value and calculate the area under the curve from the fitted blood input function for whole body CBM parametric PET based on a Patlak model, for example. This approach of tracking dynamic scans and calculating time information for parametric PET can be readily applied to different CBM scan modes and address non-uniform time sampling over different organs and different passes. This method has potential advantages over standard uptake value (SUV) images for tumor detection.

There are many kinetics models for parametric imaging. Some embodiments employ a linear Patlak model to generate two parametric images: one for metabolism rate (abbreviated as "$K_i$") and one for distribution volume (abbreviated as "$d_v$"). Clinical scanners with continuous bed motion (CBM) offer great flexibility to acquire dynamic data for parametric imaging in terms of scan range, scan direction, and scan speed. In addition to its flexibility to implement variable bed speed over different organs, CBM scan can also acquire more counts in a specific amount of time, since CBM does not waste time on bed by bed transition, during which no counts are acquired. A PET scanner with CBM capability can be used to implement multi-pass dynamic scans with sequential same direction, bi-directional, or mixed scan mode.

To calculate kinetics rate, the exemplary CBM systems record accurate time and position information. The present method provides consistent quantification results for parametric images by taking time information into account properly. In CBM volume, the imaging start time and imaging duration—which are used to pick a time point in blood input function—may vary from voxel to voxel. In the exemplary methods, start imaging time and imaging duration are calculated slice by slice to account for variable scanning speeds and a variety of different scanning modes. This disclosure provides a method to calculate time information for CBM parametric PET based on finely sampled bed tags which accurately encode position and time information of bed and apply the time information on Patlak reconstruction. The method can be readily applied to different scan modes and solve the non-uniform time sampling problem at different axial locations. Parametric images collected by these methods can be a better alternative for tumor detection.

Figure 1:
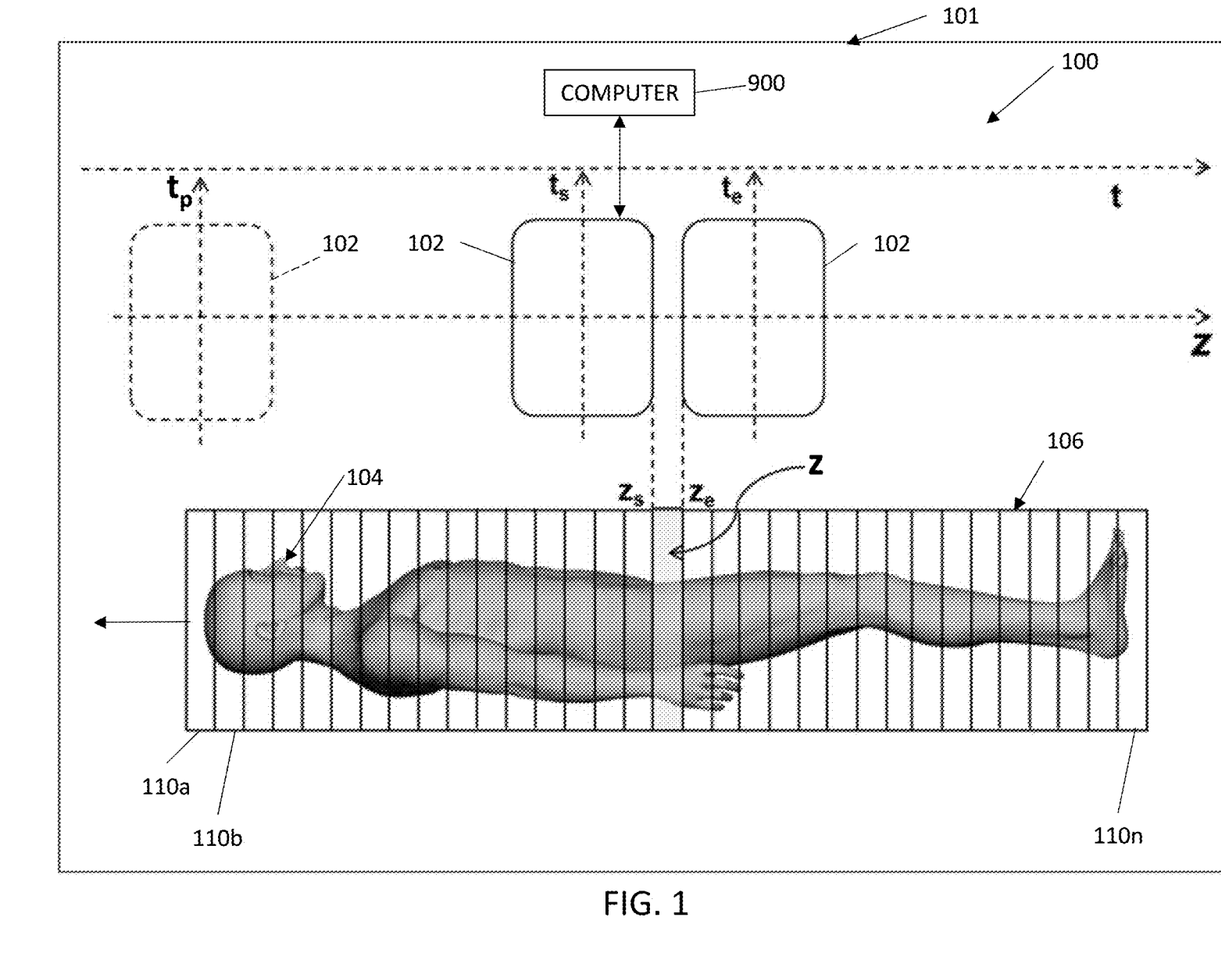
FIG. 1 is a schematic diagram of a parametric PET scanning system according to some embodiments.

FIG. 1 is a schematic view of a PET system 101 including a scanner 100, configured for CBM scanning, and a computer system 900 configured for controlling the scanner 100 and processing and reconstructing data acquired by the scanner 100. The scanner 100 includes a PET gantry 102 positioned with respect to a patient 104 on a bed 106. In some embodiments, for a slice z, the gantry 102 moves continuously from an initial position $z_s$ at an initial time $t_s$ to an end position $z_e$ at an end time $t_e$. In some embodiments, the gantry 102 is stationary and the bed 106 moves continuously past the gantry 102 from the initial position $z_s$ to the end position $z_e$. In some embodiments, $z_s$ corresponds to the head of the bed 106 and $z_e$ corresponds to a foot of the bed 106. In some embodiments, $z_s$ and/or $z_e$ may correspond to any relative position of the bed 106 with respect to the gantry 102. The gantry 102 (or bed 106) moves in increments which can vary as the relative velocity between the bed 106 and the gantry 102 varies. The scanner 100 can be a "BIOGRAPH MCT FLOW™" PET system by Siemens Medical Solutions USA, Inc. of Malvern, Pa. The computer system 900 is described below.

Figure 2:
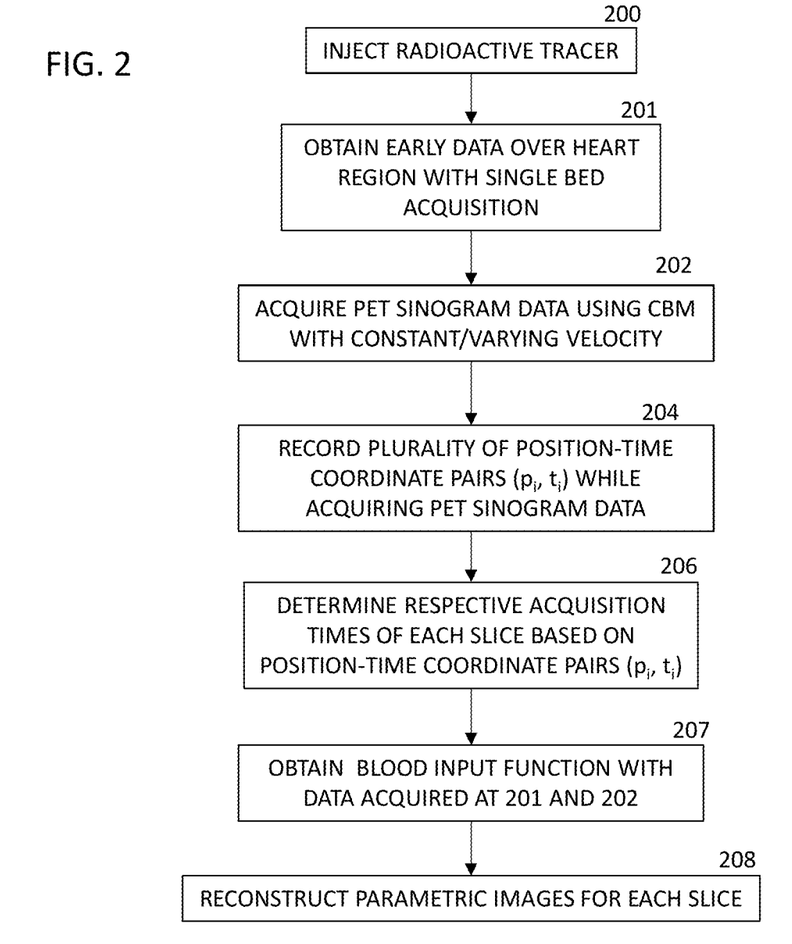
FIG. 2 is a flow chart of a method of operating the PET scanning system of FIG. 1.

FIG. 2 is a flow chart of an exemplary method of processing and reconstructing positron emission tomography (PET) dynamic sinogram data.

At step 200, a radioactive tracer material, such as fluorodeoxyglucose, is injected into the patient for functional imaging.

At step 201, the system acquires dynamic PET sinogram data over the heart region with single bed mode.

At step 202, the scanner 100 acquires PET sinogram data using continuous bed motion having a constant/varying velocity. The scanner 100 can be operated with relative motion between the bed 106 and the gantry 102 in a single-direction, multiple-pass mode, a bidirectional mode, or a mixed mode including single-directional motion during a first portion of one or more passes, and in a bidirectional mode during a second portion of the one or more passes. The velocity can vary as a continuous function of time (e.g., saw tooth or sinusoidal), or as a discontinuous function of time (e.g., an alternating step function). The velocity can have a more complex profile; for example, the acceleration (time derivative of velocity) can be a continuous function, or can have one or more discontinuities at which the acceleration jumps.

At step 204, the system 101 records a plurality of bed tags (position-time coordinate pairs) in a non-transitory, machine-readable storage medium while acquiring the PET sinogram data. For each bed tag, the position and time are determined with respect to an initial condition ($p_0$, $t_0$), such as a position $p_0$ of z=0.0 at the time $t_0$=0 when the tracer is injected. The position can be accurately determined by a position sensor (e.g., a laser interferometer or the like). In some embodiments, the bed tags are collected at even time intervals (e.g., 10 msec or 100 msec). In other embodiments, the time intervals between bed tags vary with velocity (e.g., the interval can be 100 msec while the velocity is less than a threshold value, and 10 msec while the velocity is greater than the threshold value).

At step 206, the system 101 determines respective acquisition times of each of a plurality of slices of the image, based on the plurality of position-time coordinates. In the case where the relative velocity between the bed 106 and the gantry 102 varies during the continuous bed motion, the distance between pairs of successive bed tags is not constant. Because the slices are selected to have a common thickness, the initial position $z_s$ and the end position $z_e$ of each slice generally do not coincide with the position coordinates of any of the bed tags. In various embodiments, a variety of methods can be used to select a representative acquisition time for each slice. For example, the respective time point when average activity occurs for each respective slice can be computed as the representative acquisition time for the slice. A method of determining the representative acquisition time is described below.

At step 207, the system obtains a parameterized blood input function based on the data acquired at step 201 and step 202.

At step 208, the system 101 reconstructs a respective image for each respective slice in the plurality of slices. The reference time for each slice is the representative acquisition time determined at step 206.

Figure 3:
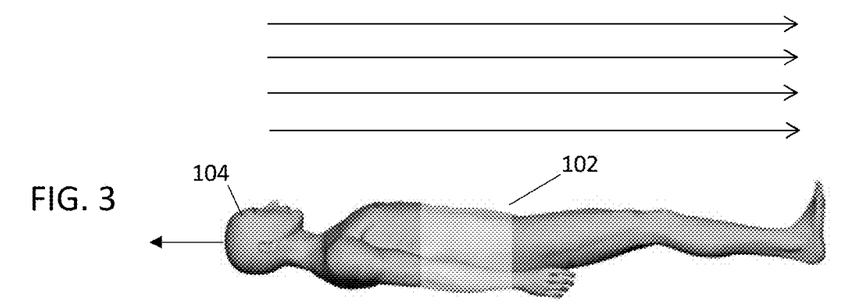
FIG. 3 is a schematic diagram showing single-direction, multiple-pass scanning mode for operating the PET scanning system of FIG. 1.
Figure 4:
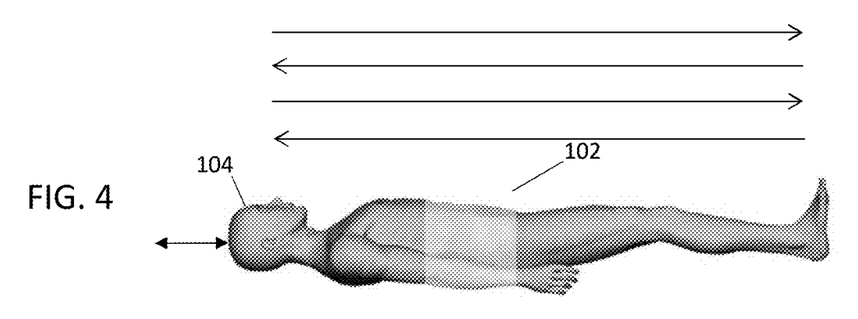
FIG. 4 is a schematic diagram showing bidirectional scanning mode for operating the PET scanning system of FIG. 1.
Figure 5:
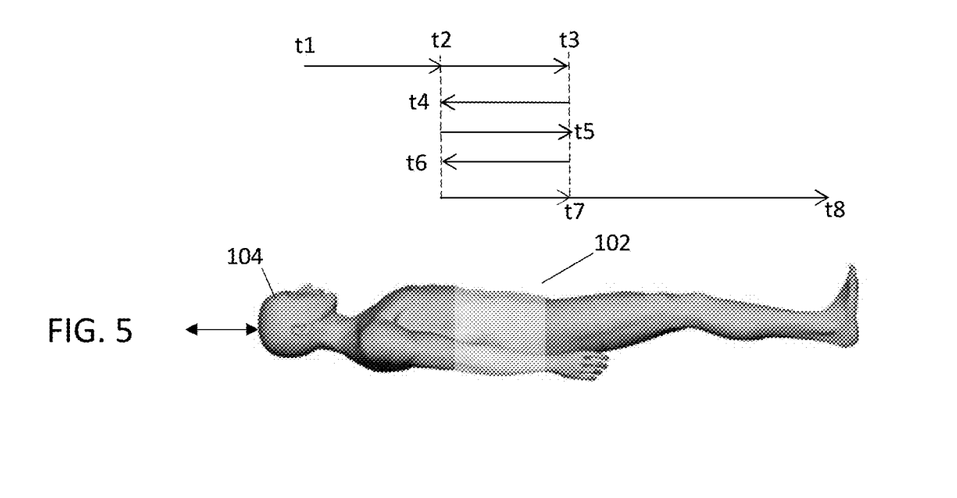
FIG. 5 is a schematic diagram showing mixed single-direction, multiple-pass and bidirectional scanning modes for operating the PET scanning system of FIG. 1.

FIGS. 3-5 show three non-limiting examples of CBM scanning modes supported by the system of FIG. 1 and the method of FIG. 2.

FIG. 3 schematically shows a single-direction, multiple pass scanning mode. According to this scanning mode, the patient 104 moves head-first through the field of view (FOV) of the gantry 102 of scanner 100, until the patient's whole body passes through the FOV. (Alternatively, the gantry 102 moves along the length of the patient's body, from head to foot.) At the end of each pass, the patient 104 (or the gantry 102) returns to its original position, and the next pass begins, with relative motion between the patient 104 and the gantry 102 in the same direction as in the preceding pass. Although FIG. 3 shows an example in which the patient moves past the FOV head-first, the patient can alternatively move past the FOV feet-first.

Figure 3A:
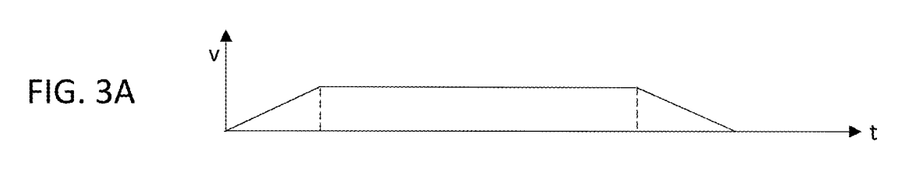
FIGS. 3A-3C show non-exclusive examples of velocity profiles for the motion of the bed in the system of FIG. 1.
Figure 3B:
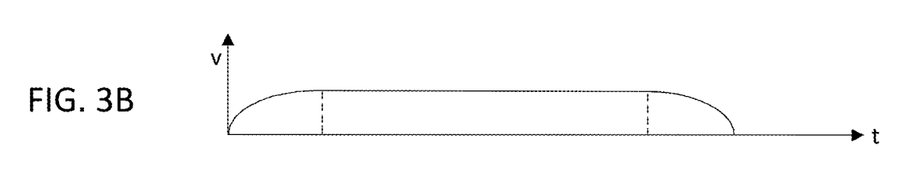
Figure 3C:
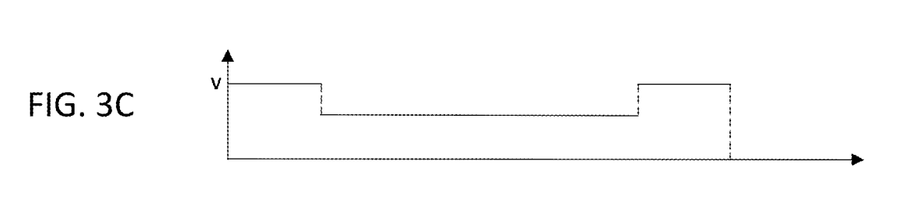

The arrows in FIG. 3 indicate direction, and roughly indicate the range of axial motion of the bed, but do not show the velocity. The velocity of the motion in FIG. 3 can vary during one or more of the passes. For example, in some embodiments, as shown in FIG. 3A, the velocity can increase linearly from zero to a maximum speed at the beginning of the pass, maintain the maximum speed in the middle of the pass, and decrease linearly to zero at the end of the pass. In other embodiments, as shown in FIG. 3B, the velocity profile has a curved shape (e.g., sinusoidal, parabolic, or logarithmic) at the beginning and end of each pass. In another example, as shown in FIG. 3C, the velocity can begin at a maximum speed, decrease to a slower speed while an organ of interest (e.g., brain, heart, liver or prostate) is within the FOV of the scanner 100, and return to the maximum speed for the remainder of the scan. The velocity profile can be the same in each pass. In another example, the scanner 100 can use two different velocity profiles in two different passes.

FIG. 4 schematically shows a bidirectional scanning mode. According to this scanning mode, the patient 104 moves head-first through the field of view (FOV) of the gantry 102 of scanner 100, until the patient's whole body passes through the FOV, and then returns foot-first through the gantry 102 while scanning. (Alternatively, the gantry 102 moves along the length of the patient's body, from head to foot, and then returns from foot to head while scanning). At the end of each even-numbered pass, the patient 104 and the gantry 102) are in their original positions, ready to repeat the back-and-forth sequence. The velocity of the motion in the mode of FIG. 4 can vary. For example, in some embodiments, as described for the mode of FIG. 3, the velocity profile may have a linear shape or a curved shape (e.g., sinusoidal, parabolic, or logarithmic) at the beginning and end of each pass. Any of the velocity profiles discussed with respect to the mode of FIG. 3-3C can be used in the mode of FIG. 4.

FIG. 5 schematically shows a mixed scanning mode, in which the constant/varying velocity includes a combination of single-direction motion over a first portion of an axial range of bed motion (t1 to t2 and/or t7 to t8) and bidirectional motion over a second portion of the axial range of bed motion (t2 to t7). According to this scanning mode, the patient 104 moves head-first in a first direction through the field of view (FOV) of the gantry 102 of scanner 100, from time t1 until time t2. (Alternatively, the gantry 102 moves along the length of the patient's body, beginning at the head). From time t2 till time t7, the patient 104 moves in bidirectional scanning mode across a second portion of the body of patient 104. From time t3 to time t4, the patient 104 (or gantry 102) reverses direction and moves part way in a second direction opposite the first direction, towards the original position. At times t5 and t6, the patient 104 (or gantry 102) again reverses direction and moves part way past the FOV. At time t7, the patient (or gantry 102) resumes single-direction scanning until the remainder of the body of patient 104 has been scanned at t8. This is only one example, and any combination of single direction and bidirectional modes can be used. The velocity can vary according to any one or more of the velocity profiles discussed above with respect to FIGS. 3-3C and 4.

Figure 6:
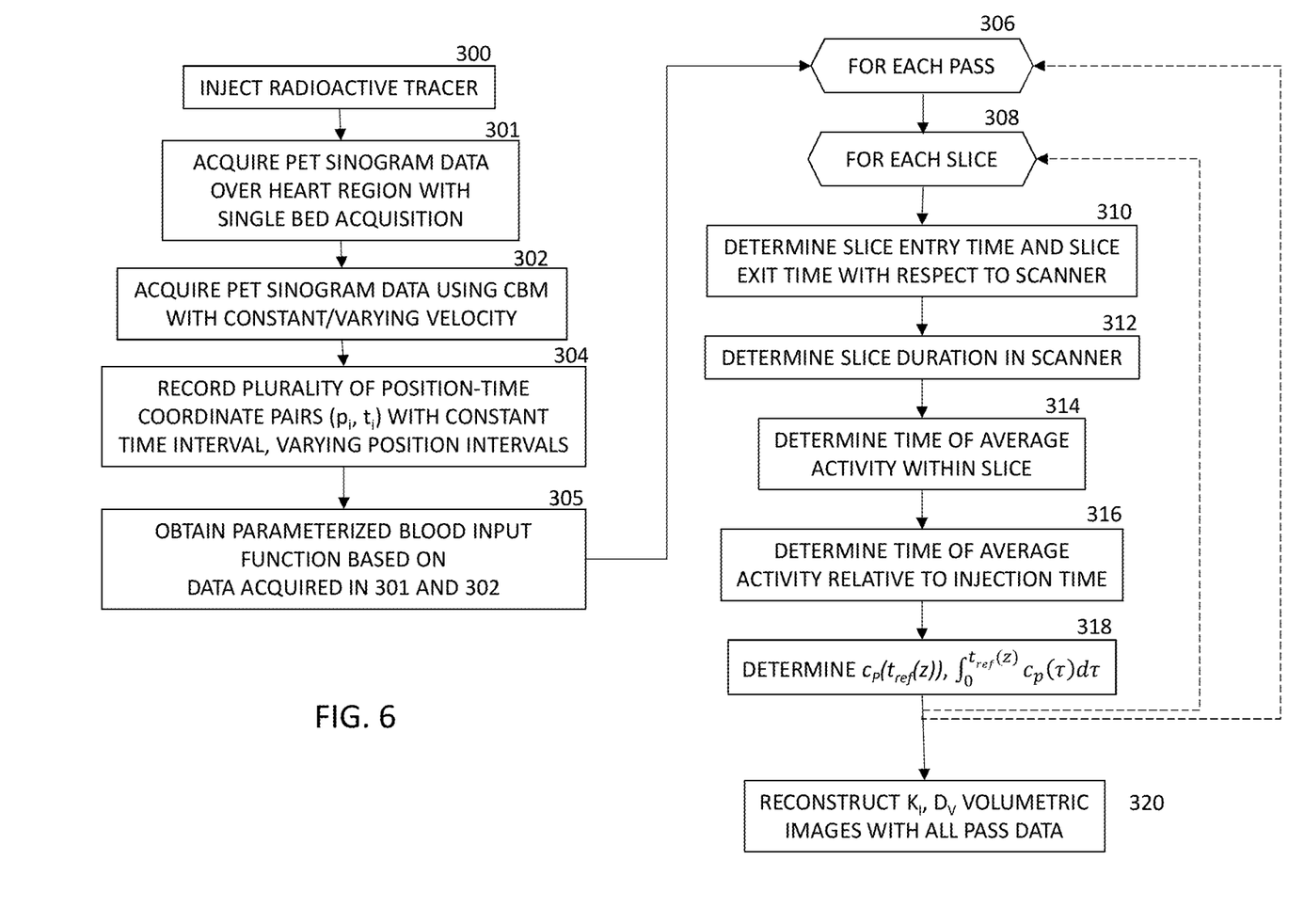
FIG. 6 is a flow chart of a method of operating the PET scanning system of FIG. 1, with details of parameter computation.

FIG. 6 is a flow chart of a detailed example of dynamic PET sinogram data acquisition, processing, and parametric image reconstruction.

At step 300, a radioactive tracer material, such as fluorodeoxyglucose, is injected into the patient for functional imaging.

At step 301, the system 101 acquires PET sinogram data over the patient's heart region with single bed mode (since one PET axial FOV is able to cover the whole heart).

At step 302, the system 101 acquires PET sinogram data using continuous bed motion having a constant/varying velocity.

At step 304, the system 101 records a plurality of bed tags (position-time coordinate pairs) in a non-transitory, machine-readable storage medium while acquiring the PET sinogram data. In this example, the bed tags are separated by a constant time interval (e.g., 100 msec). Thus, time coordinates of successive ones of the position-time coordinate pairs are separated from each other by a constant time interval, and position coordinates of the position-time coordinate pairs are separated from each other by constant/varying position intervals.

At step 305, the system 101 obtains a parameterized/fitted blood input function based on data acquired at step 301 and step 302.

At step 306, a loop containing steps 308-318 is repeated for each pass of scanner 100.

At step 308, a loop containing steps 310-318 is repeated for each image slice.

At step 310, the slice entry time $t_s$ and slice exit time $t_e$ of the slice with respect to the gantry 102 of the scanner 100 are determined, based on equations (1) and (2):

$$t_s(pass,z) = f(z_s(z), pass\ start\ time, bed\ tags, scan\ mode) \quad (1)$$

$$t_e(pass,z) = f(z_e(z), pass\ start\ time, bed\ tags, scan\ mode) \quad (2)$$

where $t_s$(pass, z) is the slice start time (relative to pass start time) when the slice centered at z enters the FOV of the scanner 100; $t_e$(pass, z) is the slice end time (relative to pass start time) when the slice centered at z exits the FOV of the scanner 100; $z_s(z)$ is the z coordinate of the starting edge of the slice; and $z_e(z)$ is the z coordinate of the ending edge of the slice, pass start time is the time (relative to injection) when the current pass starts, bed tags include time and position coordinate pairs having positions within the slice and/or nearest adjacent bed tags outside of the slice. The scan mode is one of the predetermined modes of operating the scanner 100 selected by the operator (for example, as discussed above). The function $f$ can be an interpolation function for determining the start time of the slice based on the nearest bed tags before and after the start time of the slice and the nearest bed tags before and after the end time of the slice. For example, linear, quadratic or cubic interpolation can be used.

At step 312, the slice duration $s_d$(pass, z) (i.e., the length of time the slice is within the field of view of the scanner 100) is determined, according to equation (3):

$$s_d(pass,z) = t_e(pass,z) - t_s(pass,z) \quad (3)$$

At step 314, system 101 determines a respective average acquisition time for each slice. In some embodiments, determining the average acquisition time includes determining a reference time (relative to the start time $t_s$ of the slice) when an average tracer activity of the slice occurs. This time can be computed according to equation (4).

$$tav(pass, z) = \frac{1}{\lambda} * \ln(\lambda * s_d(pass, z)/(1 - \exp(-\lambda * s_d(pass, z))) \quad (4)$$

where $t_{av}$ is the time point when average activity occurs in $s_d$ due to decay, assuming no change from kinetics; and $\lambda$ is the isotope decay constant for the injected material.

At step 316, the time of the average activity relative to injection is given by equation (5):

$$t_{ref}(pass,z) = t_s(pass,z) + tav(pass,z) \quad (5)$$

where $t_{ref}$ is the reference time; $t_s$(pass, z) is the start time of the pass relative to injection; and tav(pass,z) is the time of average activity within the slice centered at z based on equation (4).

At step 318, the system determines a respective value of a blood input function $c_p(t)$ of a patient being imaged, corresponding to the reference time for each respective slice, and a respective integral of the blood input function corresponding to each respective slice. The blood input function $c_p(t)$ is a component of a Patlak model, a technique that uses linear regression to identify and analyze pharmacokinetics of tracers involving irreversible uptake. The Patlak model is described below.

At step 320, the system reconstructs a metabolism rate $k_i$ image and a distribution volume $d_v$ image for each slice.

Some embodiments use a linear Patlak model as described in equation (6):

$$x(t) = k_i \int_0^t c_p(\tau)d\tau + d_v c_p(t), \ t > T^* \quad (6)$$

where $k_i$ is the metabolism rate (i.e., the volume of plasma from which a substance is completely removed per unit time), and $d_v$ is distribution volume (i.e., the theoretical volume that would contain the total amount of an administered drug at the same concentration observed in the blood plasma); x(t) is tissue activity in SUV, $c_p(t)$ is parameterized blood input function, and T* is the time at which the steady state of kinetics model is reached.

Dividing both sides by $C_p(t)$ provides:

$$\frac{x(t)}{c_p(t)} = k_i \frac{\int_0^t c_p(\tau)d\tau}{c_p(t)} + d_v \quad (7)$$

The unknown parameters $k_i$ and $d_v$ in equation (7) can be solved by linear regression, and their respective values at each voxel provide the $k_i$ and $d_v$ images for each slice.

Assume t=0 as injection time. After parameterization, $c_p(t)$ becomes a continuous curve that is available at any time point t>injection time. In applying the Patlak model to multi-frame dynamic data, the method uses a specific/discretized time point $t_{ref}$ for each frame, as defined by equation (5). The time $t_{ref}$ is used as frame reference or acquisition time. In CBM scanning, $t_{ref}$ is calculated at the slice level for each pass. This time point is denoted $t_{ref}(\text{pass}, z)$.

In order to calculate time information accurately for CBM scan, a plurality of bed tags $(p_i, t_i)$ are recorded into the PET dataset, where $p_i$ is the position of the bed and $t_i$ is relative time to the pass start time when $i^{th}$ tag is recorded. With bed tags, time information can be calculated for each discretized image slice centered at z for a variety of different scan modes. FIG. 6 illustrates how this time point $t_{ref}$ is calculated for each image slice in a scan pass, as described above. Equations (1) to (5) are used to obtain $t_{ref}(\text{pass}, z)$ for each slice. After $t_{ref}$ is calculated for each slice, $t_{ref}$ can be used to compute $c_p(t)$ and the integral of $c_p(t)$ for each slice from the parameterized blood input function, and subsequently be applied to the Patlak image reconstruction.

Figure 7:
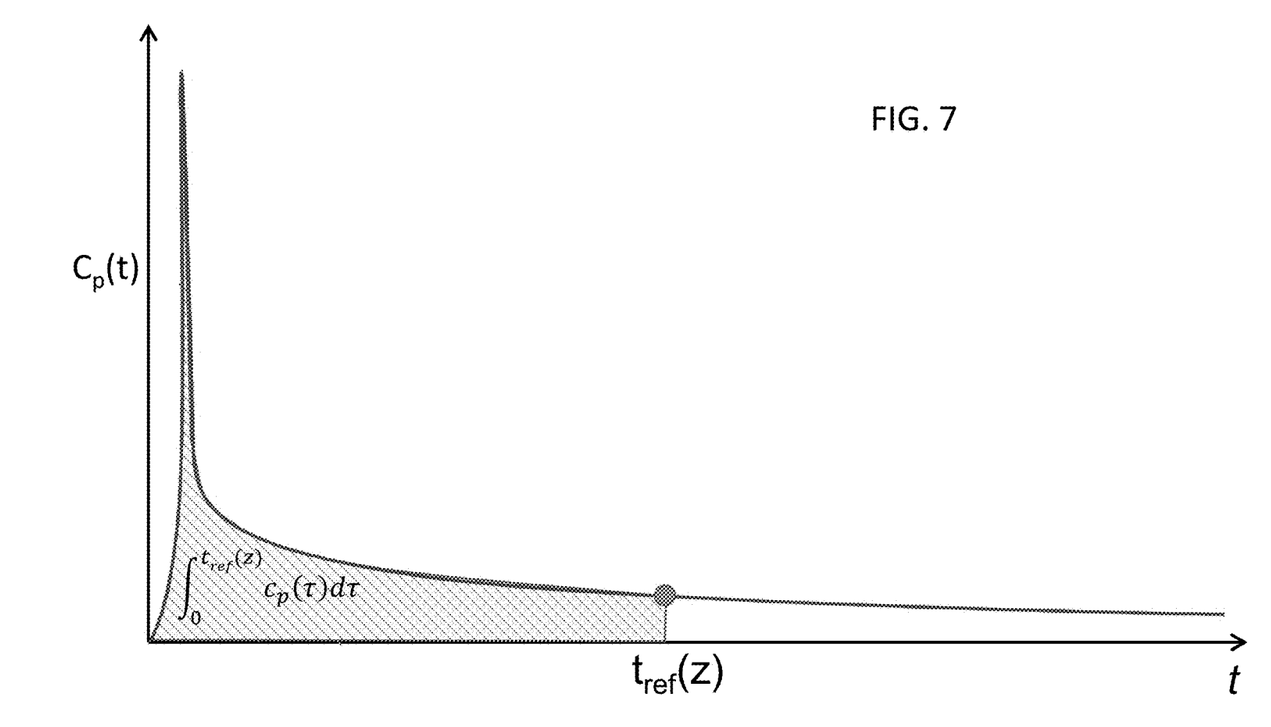
FIG. 7 is a diagram of an exemplary blood input function and its integral.

FIG. 7 shows an example of the blood intake function $c_p(t)$ and its integral $\int_0^t c_p(\tau)d\tau$. In a CBM method, different axial slices have different start imaging time and different duration. Therefore, different slices have different basis functions. The methods described above can provide a different blood input function $c_p(t)$ value and corresponding integral of the blood input function for each respective axial slice.

The calculated slice reference time can be applied to both indirect and direct parametric reconstruction. An indirect reconstruction method involves reconstructing a time series of PET images (each image reconstructed from a respective single dynamic PET frame), and then fitting a kinetic model to each voxel time activity curve (TAC). A direct reconstruction method incorporates the kinetic model into the reconstruction algorithm itself, directly producing parametric images from projection data from a complete dynamic PET dataset. Direct reconstruction methods are less sensitive to noise.

A direct reconstruction method includes direct reconstruction of parametric images from a pet image dataset having two or more image frames. The slice dependent basis functions in Patlak reconstruction can be determined from equations (8) and (9) are applied.

$$b_1(t_{ref}(\text{pass},z)) = c_p(t_{ref}(\text{pass},z)) \tag{8}$$

$$b_2(t_{ref}(\text{pass},z)) = \int_0^{t_{ref}(\text{pass},z)} c_p(\tau)d\tau \tag{9}$$

Applying these basis functions, the time-activity curve for each voxel can be modeled using the linear representations of equations (10) and (11). Each basis function corresponds to one parametric image. Basis function $b_1$ corresponds to $d_v$ image and basis function $b_2$ corresponds to $k_i$ image. A main loop includes performing multiple loops of equation (10). During each instance of executing equation (10) multiple nested loops of equation (11) are performed.

$$x_{jt} := \frac{x_{jt}(\theta_j)}{s_{jt}} \sum_i p_{ij} \frac{y_{it}}{\sum_j x_{jt}(\theta_j) + o_{it}} \tag{10}$$

$$\theta_{jk} := \frac{\theta_{jk}}{\sum_{pass} s_{jt} b_k(t_{ref}(\text{pass}, z))} \sum_{pass} s_{jt} b_k\left(t_{ref}(\text{pass}, z) \frac{x_{jt}}{x_{jt}(\theta_j)}\right)$$ (11)

where $x_{jt}$ is the time activity for a voxel, and $\theta_{jk}$ is the reconstructed value (kinetic parameter) of the $k^{th}$ parametric image at pixel j, $d_v$ is the first parametric image, $k_i$ is the second parametric image, $y_{it}$ is sinogram counts at pixel i at time t, and $s_{jt}$ is normalization factors which depend on time.

In the case of indirect reconstruction, the time-activity curve for each voxel can be modeled using the linear representations of equations (12) and (13). Equation (12) is used to reconstruct pass/frame images independently. Then post reconstruction linear fitting is performed using equation (13) over multi-frames.

$$x_{jt} := \frac{x_{jt}}{s_{jt}} \sum_i p_{ij} \frac{y_{it}}{\sum_j x_{jt} + o_{it}} \tag{12}$$

$$x_{jt} = \theta_1 b_1(t_{ref}(\text{pass}, z)) + \theta_2 b_2(t_{ref}*(\text{pass}, z)) \tag{13}$$

Figure 8A:
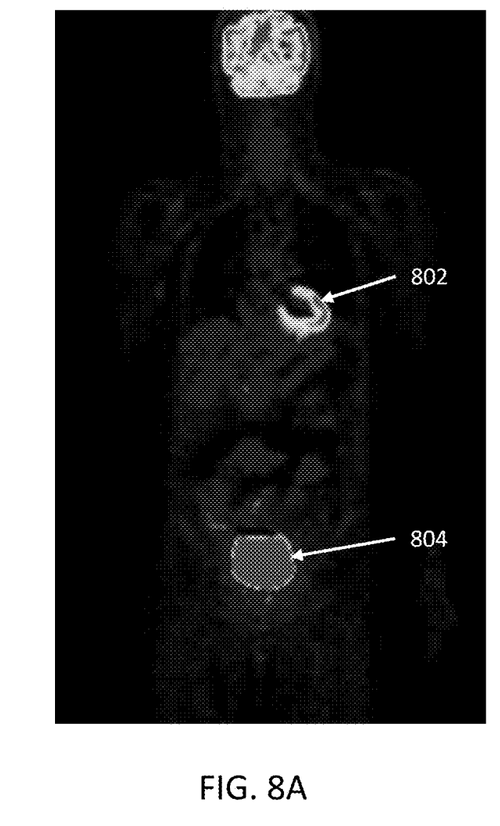
FIG. 8A is an example of a metabolism rate ($K_i$) image obtained using the system of FIG. 1 and the method of FIGS. 2 and 6.
Figure 8B:
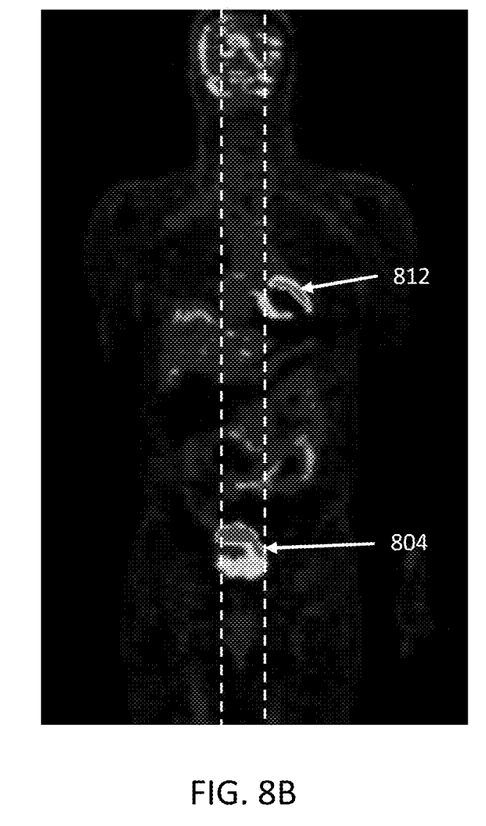
FIG. 8B is an example of a distribution volume ($d_v$) image obtained from the same subject as shown in the image of FIG. 8A.

FIG. 8A shows a $k_i$ image from a healthy control subject, and FIG. 8B shows the corresponding $d_v$ image from the same subject. Regions 802 (FIG. 8A) and 812 (FIG. 8B) show the heart activity, and regions 804 (FIG. 8A) and 814 (FIG. 8B) show the prostate activity. The hot regions around the heart 812 (FIG. 8B) and prostate 814 (FIG. 8B) in the distribution volume image (FIG. 8B) are due to patient motion. If global time is applied to the entire pass, (for example, the time from injection till the middle time point of the pass), instead of slice by slice time information as defined in equation (5), then use of the global time would result in a quantification bias in the axial direction.

Figure 8C:
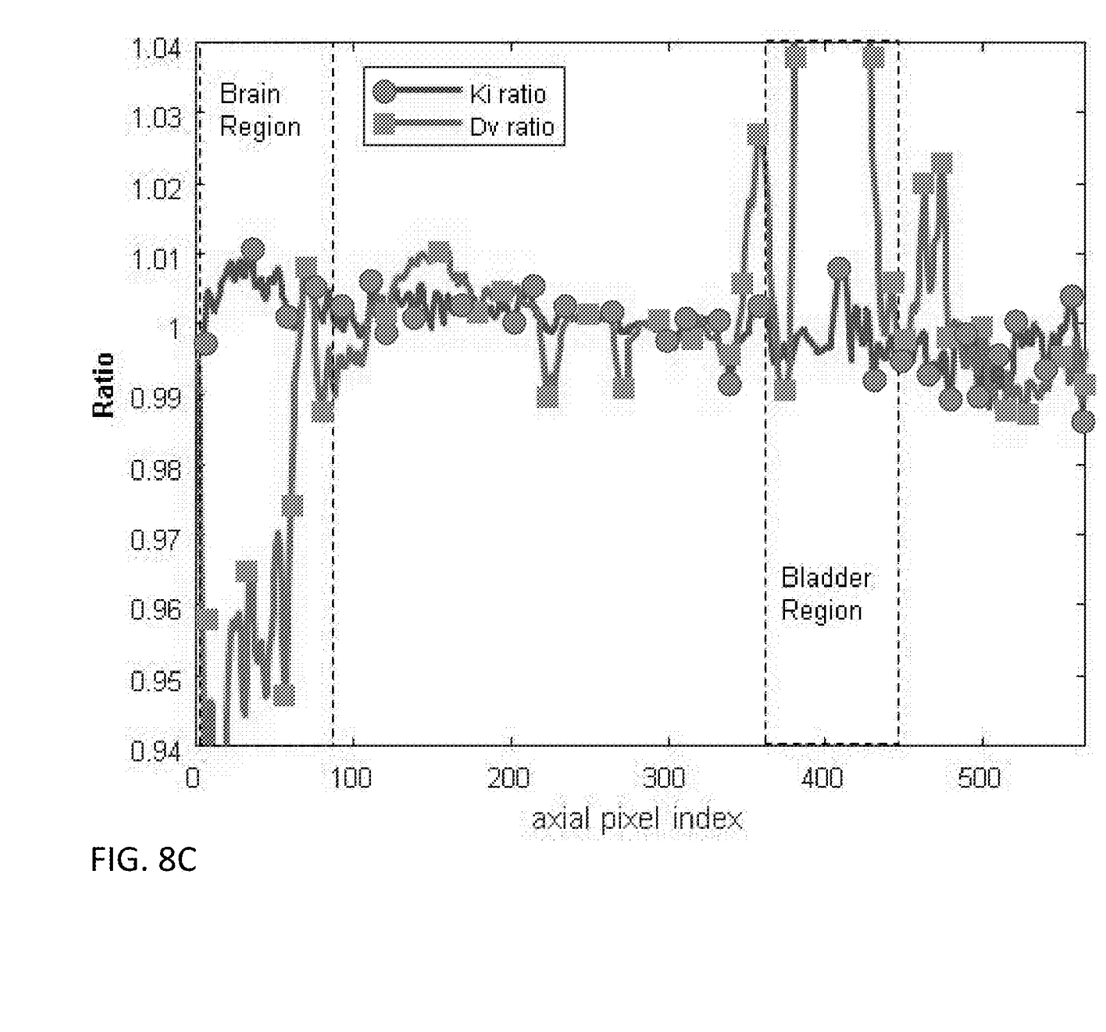
FIG. 8C is a diagram showing the bias of a model using the same pass average time for each slice, relative to the method of FIGS. 2 and 6.

FIG. 8C is a plot of the ratio between parametric images obtained by using slice by slice time information and parametric images obtained by global time. In an ideal case where there is zero bias, and both methods yield identical results, the ratio curves would be horizontal lines at Y=1.0. Any deviation from unity indicates a bias in the parametric images obtained by global time. FIG. 8C shows the axial profile plot of a 20-pixel wide region over $k_i$ and $d_v$ ratio images. The values of both $k_i$ and $d_v$ parametric images shift between using slice by slice time and global time, especially at the brain and bladder regions. This effect is more pronounced in the $d_v$ image. The amplitude of the shift will be more significant if the dynamic scan has non-uniform time sampling over different axial slices, as is likely to occur if the bed velocity varies over time and is not uniform.

Clinical scanners with CBM capability offer great potential for kinetic modeling and formation of parametric images. Accurate parametric imaging with flexible scan mode is provided. The scan time information is tracked and applied correctly. The method can accurately calculate time information for whole body CBM parametric PET based on bed tags. This approach of calculating time information based on finely-sampled bed tags can be readily applied to different scan modes and solve non-uniform time sampling problem over different axial image slices. The calculated time information can be applied for a whole-body parametric imaging using a linear Patlak model. If a global time, instead of slice by slice time information is applied to calculate basis function, inaccuracy/bias in quantification of parametric image will result. The level of resulted inaccuracy due to applying global time information depends on scan protocols, such as scan modes, and variable scan speeds over different regions of the body over different passes. Parametric images can be an alternative to SUV images for tumor detection.

Figure 9:
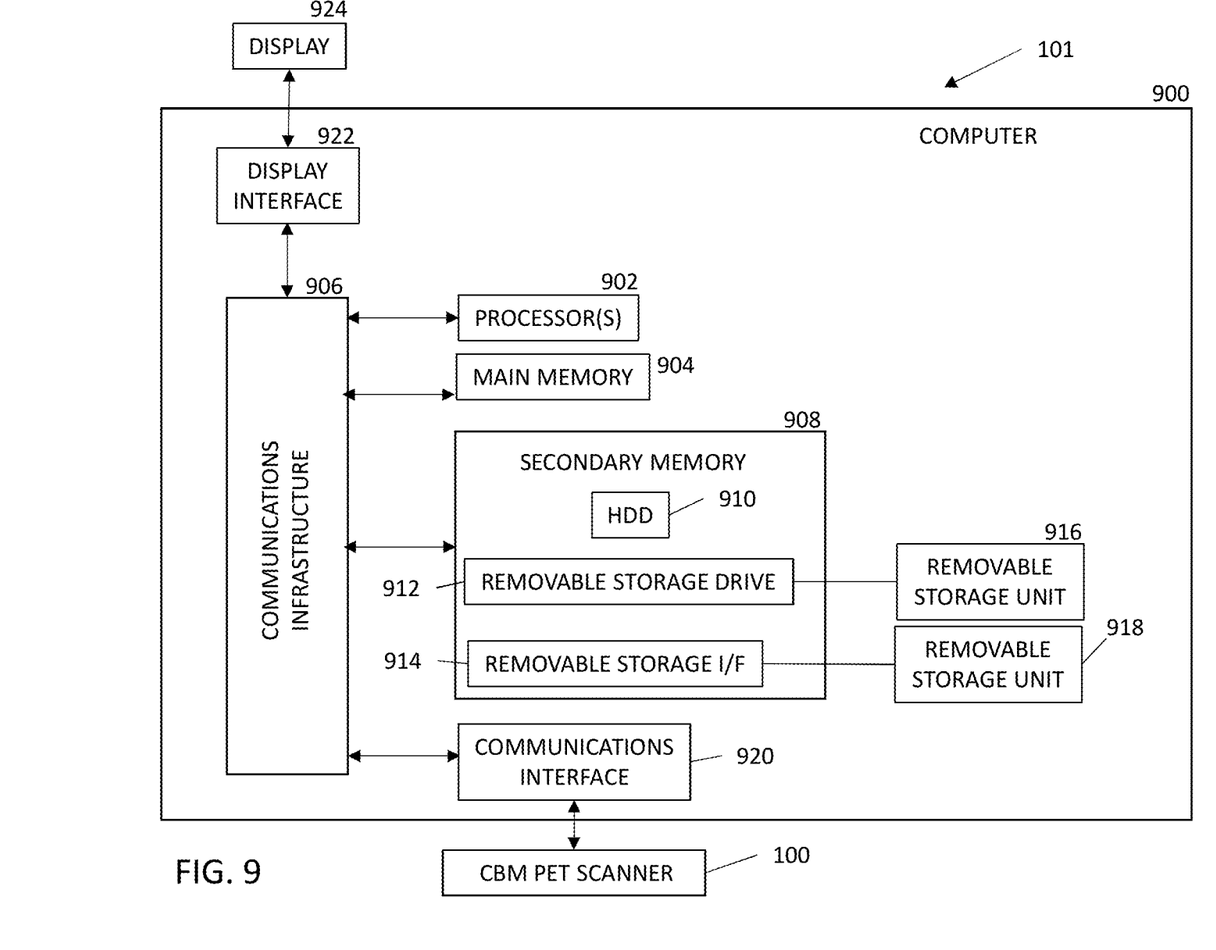
FIG. 9 is a block diagram of the system of FIG. 1, including details of the data processing system.

FIG. 9 is a block diagram of a system 101 including the scanner 100 and a computer system 900. The computer system 900 can be used in some embodiments, e.g., for implementing the processor controlling the scanner 100.

Computer system 900 may include one or more processors 902. Each processor 902 is connected to a communication infrastructure 906 (e.g., a communications bus, cross-over bar, or network). The processor 900 can be implemented as a central processing unit, an embedded processor or microcontroller, or an application-specific integrated circuit (ASIC). Computer system 900 may include a display interface 922 that forwards graphics, text, and other data from the communication infrastructure 906 (or from a frame buffer, not shown) for display on the display unit 924 to a user.

Computer system 900 may also include a main memory 904, such as a random access memory (RAM), and a secondary memory 908. The main memory 904 and/or the secondary memory 908 comprise a dynamic random access memory (DRAM). The secondary memory 908 may include, for example, a hard disk drive (HDD) 910 and/or removable storage drive 912, which may represent a solid state memory, an optical disk drive, a flash drive, a magnetic tape drive, or the like. The removable storage drive 912 reads from and/or writes to a removable storage unit 916. Removable storage unit 916 may be an optical disk, magnetic disk, floppy disk, magnetic tape, or the like. The removable storage unit 916 may include a computer readable storage medium having tangibly stored therein (or embodied thereon) data and/or computer software instructions, e.g., for causing the processor(s) to perform various operations.

In alternative embodiments, secondary memory 908 may include other devices for allowing computer programs or other instructions to be loaded into computer system 900. Secondary memory 908 may include a removable storage unit 918 and a corresponding removable storage interface 914, which may be similar to removable storage drive 912, with its own removable storage unit 916. Examples of such removable storage units include, but are not limited to, universal serial bus (USB) or flash drives, which allow software and data to be transferred from the removable storage unit 916, 918 to computer system 900.

Computer system 900 may also include a communications interface (e.g., networking interface) 920. Communications interface 920 allows instructions and data to be transferred between computer system 900 and scanner 100. Communications interface 920 also provides communications with other external devices. Examples of communications interface 920 may include a modem, Ethernet interface, wireless network interface (e.g., radio frequency, IEEE 802.11 interface, Bluetooth interface, or the like), a Personal Computer Memory Card International Association (PCMCIA) slot and card, or the like. Instructions and data transferred via communications interface 920 may be in the form of signals, which may be electronic, electromagnetic, optical, or the like that are capable of being received by communications interface 920. These signals may be provided to communications interface 920 via a communications path (e.g., channel), which may be implemented using wire, cable, fiber optics, a telephone line, a cellular link, a radio frequency (RF) link and other communication channels.

The methods and system described herein may be at least partially embodied in the form of computer-implemented processes and apparatus for practicing those processes. The disclosed methods may also be at least partially embodied in the form of tangible, non-transitory machine readable storage media encoded with computer program code. The media may include, for example, RAMs, ROMs, CD-ROMs, DVD-ROMs, BD-ROMs, hard disk drives, flash memories, or any other non-transitory machine-readable storage medium, wherein, when the computer program code is loaded into and executed by a computer, the computer becomes an apparatus for practicing the method. The methods may also be at least partially embodied in the form of a computer into which computer program code is loaded and/or executed, such that, the computer becomes a special purpose computer for practicing the methods. When implemented on a general-purpose processor, the computer program code segments configure the processor to create specific logic circuits. The methods may alternatively be at least partially embodied in a digital signal processor formed of application specific integrated circuits for performing the methods.

Figure 10A:
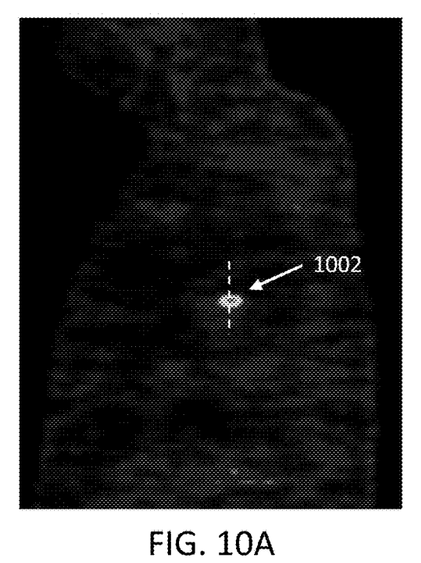
FIGS. 10A-10C show an example which demonstrates advantages of using parametric images to detect a tumor over using traditional SUV images.
Figure 10B:
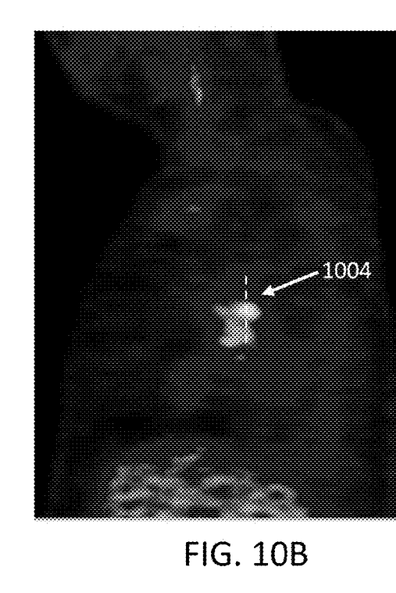
Figure 10C:
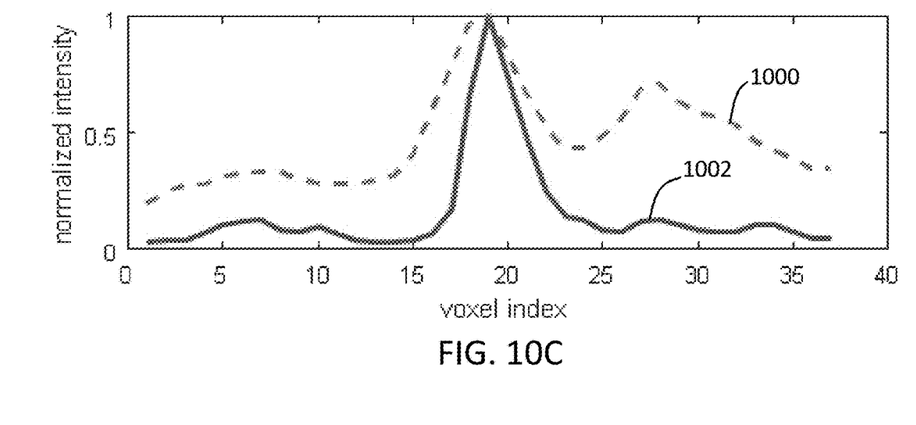

FIGS. 10A-10C show an example which demonstrates advantages of using parametric images obtained by a CBM PET system 101 to detect tumors, over using traditional SUV image. FIG. 10A is a sagittal image of $k_i$ image, FIG. 10B is a sagittal image of SUV image. The tumor (1002 and 1004) in the chest is more conspicuous in the parametric $k_i$ image, which is also shown in the line plot over the tumor FIG. 10C, in which the dashed curve 1000 indicates an image acquired using SUV and the solid curve 1002 indicates $k_i$. The signal to background ratio is much higher in the $k_i$ image in solid curve 1002.

Although the subject matter has been described in terms of exemplary embodiments, it is not limited thereto. Rather, the appended claims should be construed broadly, to include other variants and embodiments, which may be made by those skilled in the art.

What is claimed is:

1. A method of processing and reconstructing dynamic positron emission tomography (PET) sinogram data, comprising:
   acquiring PET sinogram data using continuous bed motion having a varying velocity;
   recording a plurality of position-time coordinate pairs while acquiring the PET sinogram data;
   determining respective slice acquisition times of each of a plurality of slices of an image, based on the plurality of position-time coordinate pairs;
   calculating a respective value of a blood input function and an integral of the blood input function for each respective slice acquisition time; and
   reconstructing respective parametric images for each respective slice in the plurality of slices based on the respective slice acquisition times, the respective value of the blood input function, and the integral of the blood input function of each of the plurality of slices in the image,
   wherein determining the respective slice acquisition time for each slice includes determining a reference time when an average tracer activity of the slice occurs, and
   wherein the respective value of the blood input function corresponds to the reference time when the average tracer activity occurs for each respective slice.

2. The method of processing and reconstructing dynamic PET sinogram data according to claim 1, further comprising:
   injecting radioactive tracer into a human body, and then acquiring PET sinogram data over a heart region using single bed mode, between the injecting and using continuous bed motion.

3. The method of processing and reconstructing dynamic PET sinogram data according to claim 1, further comprising obtaining a blood input function from a single bed acquisition and the sinogram data acquired using continuous bed motion, wherein the blood input function from the single bed acquisition and the sinogram data is used to calculate the respective value of the blood input function and the integral of the blood input function for each respective slice acquisition time.

4. The method of processing and reconstructing dynamic PET sinogram data according to claim 1, wherein the parametric images include a metabolism rate image and a distribution volume image.

5. The method of processing and reconstructing dynamic PET sinogram data according to claim 1, wherein time coordinates of successive ones of the position-time coordinate pairs are separated from each other by a constant time interval.

6. The method of processing and reconstructing dynamic PET sinogram data according to claim 5, wherein position coordinates of the position-time coordinate pairs are separated from each other by varying position intervals.

7. The method of processing and reconstructing dynamic PET sinogram data according to claim 1, wherein the continuous bed motion having the varying velocity includes same-direction, multi-pass motion.

8. The method of processing and reconstructing dynamic PET sinogram data according to claim 1, wherein the continuous bed motion having the varying velocity includes bidirectional motion.

9. The method of processing and reconstructing dynamic PET sinogram data according to claim 1, wherein the continuous bed motion having the varying velocity includes a combination of single-direction motion over a first portion of an axial range of bed motion and bidirectional motion over a second portion of the axial range of bed motion.

10. The method of processing and reconstructing dynamic PET sinogram data according to claim 1, wherein reconstructing the respective parametric images includes direct reconstruction of parametric images from a PET sinogram dataset having two or more dynamic frames.

11. A system for processing and reconstructing dynamic positron emission tomography (PET) sinogram data, comprising:
a processor capable of executing instructions; and
a non-transitory, machine-readable storage medium encoded with program code and coupled to the processor, the storage medium comprising:
code for controlling a PET scanner to acquire PET sinogram data using continuous bed motion having a varying velocity;
code for recording a plurality of position-time coordinate pairs while the PET scanner acquires the PET sinogram data;
code for determining respective acquisition times of each of a plurality of slices of an image, based on the plurality of position-time coordinates, wherein the code for determining the respective acquisition time for each slice includes code for determining a reference time when an average tracer activity of the slice occurs;
code for calculating a respective value of a blood input function and an integral of the blood input function for each respective slice acquisition time; and
code for reconstructing respective parametric images for each respective slice in the plurality of slices based on the respective slice acquisition times, the respective value of the blood input function, and the integral of the blood input function of each of the plurality of slices in the image,
wherein determining the respective slice acquisition time for each slice includes determining a reference time when an average tracer activity of the slice occurs, and
wherein the respective value of the blood input function corresponds to the reference time when an average tracer activity occurs for each respective slice.

12. The system for processing and reconstructing dynamic PET sinogram data according to claim 11, wherein the code for controlling configures the processor so that time coordinates of successive ones of the position-time coordinate pairs are separated from each other by a constant time interval.

13. The system for processing and reconstructing dynamic PET sinogram data according to claim 12, wherein the code for controlling configures the processor so that position coordinates of the position-time coordinate pairs are separated from each other by a varying position intervals.

14. A non-transitory, machine-readable storage medium encoded with program code for processing and reconstructing dynamic positron emission tomography (PET) sinogram data, comprising:
code for controlling a PET scanner to acquire PET sinogram data using continuous bed motion having a varying velocity;
code for recording a plurality of position-time coordinate pairs while the PET scanner acquires the PET sinogram data;
code for determining respective acquisition times of each of a plurality of slices of an image, based on the plurality of position-time coordinates, wherein the code for determining the respective acquisition time for each slice includes code for determining a reference time when an average tracer activity of the slice occurs;
code for calculating a respective value of a blood input function and an integral of the blood input function for each respective slice acquisition time; and
code for reconstructing respective parametric images for each respective slice in the plurality of slices based on the respective acquisition times, the respective value of the blood input function, and the integral of the blood input function of each of the plurality of slices in the image,
wherein determining the respective slice acquisition time for each slice includes determining a reference time when an average tracer activity of the slice occurs, and
wherein the respective value of the blood input function corresponds to the reference time when the average tracer activity occurs for each respective slice.

15. The non-transitory, machine-readable storage medium encoded with program code for processing and reconstructing dynamic PET sinogram data according to claim 14, wherein the code for control is for configuring the processor so that position coordinates of the position-time coordinate pairs are separated from each other by a varying position intervals.

* * * * *